United States Patent [19]

Seebach et al.

[11] Patent Number: 6,162,933

[45] Date of Patent: Dec. 19, 2000

[54] PROCESS FOR THE PREPARATION OF AMIDO ACID PHENYL ESTERS

[75] Inventors: Michael Seebach, Hattersheim; Peter Naumann, Taunusstein; Werner Janitschek, Kelkheim, all of Germany

[73] Assignee: Clariant GmbH, Frankfurt, Germany

[21] Appl. No.: 09/364,635

[22] Filed: Jul. 30, 1999

[30]    Foreign Application Priority Data

Jul. 31, 1998 [DE] Germany ............................ 198 34 567
Dec. 18, 1998 [DE] Germany ............................ 198 58 660

[51] Int. Cl.⁷ .................................................. C07C 231/12
[52] U.S. Cl. ................................ 554/68; 554/45; 560/41; 560/142
[58] Field of Search ......................... 554/68, 45; 560/41, 560/142

[56]    References Cited

U.S. PATENT DOCUMENTS 5,466,840  11/1995  Lutz et al. .
5,523,434   6/1996  Burns et al. .

FOREIGN PATENT DOCUMENTS

WO 96/39378  12/1996  WIPO .

*Primary Examiner*—Paul J. Killos
*Attorney, Agent, or Firm*—Miles B. Dearth; Scott E. Hanf

[57]    ABSTRACT

A process for the preparation of amido acid phenyl esters of the formula

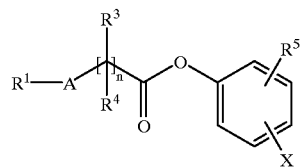

(I)

by reaction of a compound of the formula

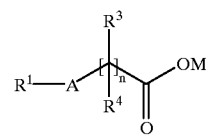

with a compound of the formula

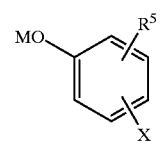

in the presence of an acid halide, where A, $R^1$, $R^2$, $R^3$, $R^4$, $R^5$, X and M are as defined in the description, is claimed. The resulting amido acid phenyl esters are used as bleach activators in detergents and cleaners.

10 Claims, No Drawings

PROCESS FOR THE PREPARATION OF AMIDO ACID PHENYL ESTERS

BACKGROUND OF THE INVENTION

The invention relates to the synthesis of amido acid phenyl esters by single-stage reaction of amidocarboxylic acids with inorganic acid halides and a phenol derivative.

Amido acid phenyl esters are used as bleach activators in detergents and cleaners. They permit a bleaching action at temperatures below 60° C. by reacting with a source of hydrogen peroxide, in most cases perborate or percarbonates, to liberate an organic peroxy acid.

The patent literature describes various processes for the syntheses of these bleach activators.

For example, U.S. Pat. No. 5,523,434 describes the preparation of amido acid phenyl esters from amidocarboxylic acids and phenolsulfonates by a two-stage process: in the first stage, an amidocarboxylic acid chloride is synthesized by reaction of the amidocarboxylic acid with inorganic acid chlorides, and in a second step, the amidocarboxylic acid chloride is reacted with a phenolsulfonate in a water/diethyl ether mixture. Problems associated with the industrial applicability of this process are the use of diethyl ether as solvent, the low storage stability of the amidocarboxylic acid chloride and the use of large excesses of inorganic acid chloride.

U.S. Pat. No. 5,466,840 likewise describes a multistage process for the synthesis of amido acid phenyl ester sulfonates. It involves reacting the alkali metal salt of a 4-hydroxybenzenesulfonic acid with a $C_2$–$C_4$-carboxylic anhydride to give the alkali metal salt of a 4-acyloxybenzenesulfonic acid. In a second stage, the latter is converted to the amido acid phenyl ester sulfonate by addition of 1-oxyalkanoylaminocarboxylic acid in the presence of a transesterification catalyst at from 150 to 250° C. over the course of from 0.5 to 10 hours. A disadvantage of both synthesis routes is that they require two or more reaction stages with intermediates which in some cases are not very stable. The formation of by-products, yield losses and laborious purification processes for the products increase the cost of the preparation of this class of compound, which is used as bleach activators in detergents and cleaners.

The process according to WO 96/39378 involves introducing amidocarboxylic acid and a phenol derivative into sulfolane, dropwise addition of a carboxylic anydride, for example acetic anhydride, and achieving conversion to amido acid phenyl ester sulfonates by heating to about 170° C. over the course of from 0.5 to 10 hours depending on the starting compound.

Unsatisfactory aspects are the very high expenditure of energy while carrying out the reaction, reduced yields, heavily contaminated products and the very laborious and costly removal of the high-boiling solvent. The object was therefore to find an improved procedure for the preparation of amido acid phenyl ester sulfonates.

SUMMARY OF THE INVENTION

Surprisingly, it has been found that the slow dropwise addition of thionyl chloride at 50 to 80° C. to a reaction mixture of amidocarboxylic acid and phenolsulfonate or a phenol derivative in a low-boiling solvent, for example in n-butyl acetate, in a one-pot process gives amido acid phenyl ester sulfonates in very pure form and in high yields. Advantageous aspects are a significantly lower expenditure of energy than in the current processes and the simple removal of the solvent by distillation or by precipitating out the reaction product.

The invention provides a process for the synthesis of amido acid phenyl esters of the formula I

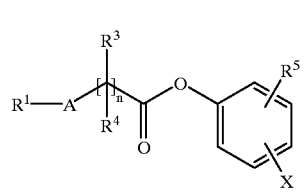

where

A is a group of the formula —$CONR^2$— or —$NR^2CO$—, $R^1$ is an alkyl, alkenyl, alkynyl or cycloalkyl group having in each case from 1 to 26 carbon atoms, or an aryl or alkylaryl group having in each case from 6 to 14 carbon atoms, $R^2$ is hydrogen or an alkyl, alkenyl, alkynyl or a cycloalkyl group having in each case from 1 to 26 carbon atoms, or an aryl or alkylaryl group having in each case from 6 to 14 carbon atoms, $R^3$ and $R^4$ may be identical or different and can each be hydrogen or an alkyl, alkenyl, alkynyl or a cycloalkyl group having in each case from 1 to 10 carbon atoms, $R^5$ is hydrogen, halogen or an alkyl, alkenyl, alkynyl, cycloalkyl or an alkoxy group having in each case from 1 to 6 carbon atoms, n is a number from 1 to 10, X is a group of the formulae $SO_3M$, $OSO_3M$, $(CH_2)_m SO_3M$, $(CH_2)_m$—$OSO_3M$, $CO_2M$ and $N(R^6)_3Y$, where M is hydrogen or an alkali metal ion, $R^6$ is an alkyl group having from 1 to 6 carbon atoms or a cycloalkyl group having from 4 to 6 carbon atoms, Y is a halogen atom and m is 1 or 2.

DESCRIPTION OF THE PREFERRED EMBODIMENTS

Preference is given to the preparation of compounds of the formula (I) where at the same time A is a group of the formula —$CONR^2$—, $R^1$ is $C_8$–$C_{10}$—alkyl, $R^2$, $R^3$, $R^4$ and $R^5$ are hydrogen, n=5 and X is —$SO_3M$.

This process involves adding an inorganic acid halide to a mixture of the compounds of the formulae II and III

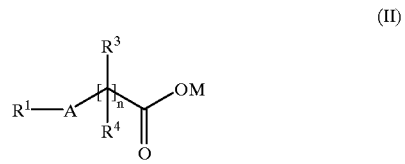

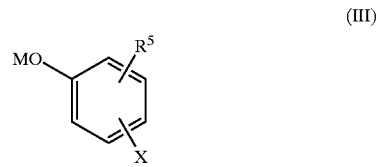

where A, $R^1$, $R^2$, $R^3$, $R^4$, $R^5$ and M are as defined above.

In detail, the process of the invention is carried out by firstly dissolving or suspending the two starting compounds of the formulae II and III together in a suitable organic solvent. Examples of suitable solvents are xylene, benzene, monoglyme, diglyme, diisopropyl ether, tetrahydrofuran, dioxane, isobutyl methyl ketone, acetone, diethyl ketone, acetonitrile, carboxylic alkyl esters or mixtures thereof. Examples of carboxylic alkyl esters are acetic acid $C_2$–$C_4$-alkyl esters, such as n-propyl acetate, i-propyl acetate, n-butyl acetate, i-butyl acetate, t-butyl acetate or mixtures thereof. Preference is given to toluene or n-butyl acetate. The molar ratio of the compounds of the formulae II and III is 1:0.7 to 1.5, preferably 1:0.8 to 1.3.

To this solution or suspension of the compounds II and III is added an inorganic acid halide, for example $PCl_3$, $PCl_5$, $POCl_3$, $COCl_2$, preferably $SOCl_2$. In place of these chlorides, it is also possible to use the analogous bromides. The amount of acid halide is from 0.5 to 2, preferably from 0.7 to 1.5, in particular from 0.9 to 1.4, molar equivalents, based on the amidocarboxylic acid. The temperature at which the reaction is carried out is generally from 25 to 120° C., preferably from 50 to 110°C., particularly preferably from 60 to 100° C.

The reaction is complete within a period of from 10 minutes to 8 hours, preferably from 30 minutes to 5 hours, and is followed by a post-stirring time of from 10 minutes to 5 hours, preferably from 30 minutes to 3 hours.

When the reaction is complete, the solvent used can be removed from the reaction product by distillation, decantation or siphonage. After dilution with water, the reaction mixture is adjusted to a pH of pH 4 to pH 11, preferably pH 7 to pH 10 by addition of a base, preferably sodium hydroxide solution, potassium hydroxide solution, sodium carbonate or potassium carbonate. The resulting end products can be separated off from this mother liquor by filtration, suction filtration, decantation or by centrifugation. For purification, the moist product can be stirred with or recrystallized from water, alcohols, aromatic solvents, alkanes, ketones or esters, and mixtures thereof, preferably water, alcohols or esters or mixtures thereof.

Using the synthesis process of the invention, the target compound is obtained in yields above 80% and high purity (content of amido acid phenyl ester above 90%).

The examples below serve to illustrate the invention in more detail without limiting it thereto.

EXAMPLES

Examples 1 to 7 illustrate the synthesis of n-nonanoylamidocaproyloxybenzenesulfonic acid, sodium salt using various solvents and conditions during work-up.

1. Synthesis of n-nonanoylamidocaproyloxybenzenesulfonic acid, sodium salt in toluene 135.7 g (0.5 mol) of n-nonanoylamidohexanoic acid and 100.1 g (0.5 mol) of p-phenolsulfonic acid, sodium salt (98%) were suspended in 600 ml of toluene and heated to 80° C. Over the course of 3 hours, 77.4 g (0.65 mol) of thionyl chloride were added dropwise to this mixture, which was then stirred for 2 hours at 80° C. Then, about 250 ml of toluene were distilled off under reduced pressure and at 30 to 40° C., and 1000 ml of water were added with vigorous stirring. 78 g of sodium hydroxide solution (32%) were added dropwise to adjust the pH to 8.0 to 8.5. The product which precipitated out was filtered off with suction, washed with 2×100 ml of water and dried overnight at 50°C. in a vacuum drying cabinet. This gave 189.2 g (84%) of n-nonanoylamidocaproyloxybenzenesulfonic acid, sodium salt as a beige-white solid. The following analytical data for the product were determined by means of HPLC:

94.0% of n-nonanoylamidocaproyloxybenzenesulfonic acid, sodium salt 0.9% of n-nonanoylamidohexanoic acid 0.4% of p-phenolsulfonic acid, sodium salt 0.7% of nonanoyloxybenzenesulfonic acid, sodium salt 2. Synthesis of n-nonanoylamidocaproyloxybenzenesulfonic acid, sodium salt in toluene without distillation of the solvent 135.7 g (0.5 mol) of n-nonanoylamidohexanoic acid and 100.1 g (0.5 mol) of p-phenolsulfonic acid, sodium salt (98%) were suspended in 750 ml of toluene and heated to 80° C. Over the course of 4 hours, 77.4 g (0.65 mol) of thionyl chloride were added dropwise to this mixture, which was then stirred for 2 hours at 80° C. Most of the toluene phase was then separated off by decantation and siphoning, and the residue was diluted with 500 ml of water. 119 g of sodium hydroxide solution (32%) were added dropwise to adjust the pH to 9.0. The product which precipitated out was filtered off with suction, washed with 2×100 ml of water and dried overnight at 50° C. in a vacuum drying cabinet. This gave 192.0 g (85.4%) of n-nonanoylamidocaproyloxybenzenesulfonic acid, sodium salt as a white solid. The following analytical data for the product were determined by means of HPLC:

93.5% of n-nonanoylamidocaproyloxybenzenesulfonic acid, sodium salt 1.6% of n-nonanoylamidohexanoic acid 0.2% of p-phenolsulfonic acid, sodium salt 0.7% of nonanoyloxybenzenesulfonic acid, sodium salt 3. Synthesis of n-nonanoylamidocaproyloxybenzenesulfonic acid, sodium salt in diisopropyl ether 67.85 g (0.25 mol) of n-nonanoylamidohexanoic acid and 50.05 g (0.25 mol) of p-phenolsulfonic acid, sodium salt (98%) were suspended in 370 ml of diisopropyl ether and heated to 69° C. Over the course of 3 hours, 37.2 g (0.313 mol) of thionyl chloride were added to this mixture under reflux, and the mixture was then stirred for a further 2 hours at reflux. Then, about 200 ml of ether were distilled off under reduced pressure and at 30 to 40° C., and 750 ml of water were added with vigorous stirring. 52 g of sodium hydroxide solution (32%) were added dropwise to adjust the pH to 8.6. The product which had precipitated out was filtered off with suction, washed with 2×50 ml of water and dried overnight at 50° C. in a vacuum drying cabinet. This gave 98.7 g (88%) of n-nonanoylamidocaproyloxybenzenesulfonic acid, sodium salt as a beige-white solid. The following analytical data for the product were determined by means of HPLC:

91.7% of n-nonanoylamidocaproyloxybenzenesulfonic acid, sodium salt 1.2% of n-nonanoylamidohexanoic acid 0.1% of p-phenolsulfonic acid, sodium salt 0.8% of nonanoyloxybenzenesulfonic acid, sodium salt 4. Synthesis of n-nonanoylamidocaproyloxybenzenesulfonic acid, sodium salt in toluene and subsequent work-up by stirring in water 67.85 g (0.25 mol) of n-nonanoylamidohexanoic acid and 50.05 g (0.25 mol) of p-phenolsulfonic acid, sodium salt (98%) were suspended in 370 ml of toluene and heated to 75° C. Over the course of 3 hours, 37.2 g (0.313 mol) of thionyl chloride were added dropwise to this mixture under reflux, and the mixture was then stirred for a further 2 hours at reflux. Then, about 117 ml of toluene were distilled off under reduced pressure and at 30° C., and 750 ml of water were added. 41.3 g of sodium hydroxide solution (32%) were added dropwise to adjust the pH to 8.5. After the mixture had been stirred for a further 30 minutes, the product which had precipitated out was filtered off with suction and stirred for one hour with 300 ml of water at 40° C. After the mixture had cooled, it was again filtered with suction, and the product was dried overnight at 50° C. in a vacuum drying cabinet. This gave 93.1 g (83%) of n-nonanoylamidocaproyloxybenzenesulfonic acid, sodium salt as a white solid. The following analytical data for the product were determined by means of HPLC:

98.4% of n-nonanoylamidocaproyloxybenzenesulfonic acid, sodium salt 0.3% of n-nonanoylamidohexanoic acid 0.1% of p-phenolsulfonic acid, sodium salt 0.1% of nonanoyloxybenzenesulfonic acid, sodium salt Comparison with the analytical data from Example 1 proves that it is possible to achieve an additional purification effect without significant yield losses by stirring out.

5. Synthesis of n-nonanoylamidocaproyloxybenzenesulfonic acid, sodium salt in n-butyl acetate 135.7 g (0.5 mol) of n-nonanoylamidohexanoic acid and 100.1 g (0.5 mol) of p-phenolsulfonic acid, sodium salt (98%) were suspended in 600 ml of toluene and heated to 90° C. under an $N_2$ atmosphere. Over the course of 3 hours, 77.4 g (0.65 mol) of thionyl chloride were added dropwise to this mixture, which was then stirred for a further 1 hour at 90° C. After the mixture had cooled to 30° C., 900 ml of water were added with vigorous stirring. 128 g of sodium hydroxide solution (32%) were added dropwise at a temperature of 35 to 40° C. to adjust the pH to 8.0. The product which had precipitated out was cooled to 20° C. and filtered off with suction, washed once with 100 ml of water and dried overnight at 60° C. in a vacuum drying cabinet. This gave 198.6 g (88.3%) of n-nonanoylamidocaproyloxybenzenesulfonic acid, sodium salt as a beige-white solid. The following analytical data for the product were determined by means of HPLC:

92.7% of n-nonanoylamidocaproyloxybenzenesulfonic acid, sodium salt 0.7% of n-nonanoylamidohexanoic acid 0.7% of p-phenolsulfonic acid, sodium salt 0.3% of nonanoyloxybenzenesulfonic acid, sodium salt 6. Synthesis of n-nonanoylamidocaproyloxybenzenesulfonic acid, sodium salt in isopropyl acetate 135.7 g of n-nonanoylamidohexanoic acid and 101.1 g of p-phenolsulfonic acid, sodium salt (98%) were suspended in 300 ml of isopropyl acetate and heated to 80° C. Over the course of 3 hours, 77.4 g of thionyl chloride were added dropwise to this mixture, which was then stirred for a further hour at 80° C. After the mixture had cooled to room temperature, 700 ml of water were added, and 109 g of sodium hydroxide solution (32%) were added dropwise to adjust the pH to 7.5 to 8.0. The product which had precipitated out was filtered off with suction and dried overnight at 60° C. in a vacuum drying cabinet. This gave 200.0 g (89%) of n-nonanoylamidocaproyloxybenzenesulfonic acid, sodium salt as a white solid. The following analytical data for the product were determined by means of HPLC:

92.3% of n-nonanoylamidocaproyloxybenzenesulfonic acid, sodium salt 1.1% of n-nonanoylamidohexanoic acid 0.4% of p-phenolsulfonic acid, sodium salt 1.0% of nonanoyloxybenzenesulfonic acid, sodium salt 7. Synthesis of n-nonanoylamidocaproyloxybenzenesulfonic acid, Na salt in isobutyl acetate 135.7 g of n-nonanoylamidohexanoic acid and 100.9 g of p-phenolsulfonic acid, sodium salt (98%) were suspended in 300 ml of isobutyl acetate and heated to 90 to 95° C. Over the course of 3 hours, 77.6 g of thionyl chloride were added dropwise to this mixture, which was then stirred for a further hour at 90° C. After the mixture had cooled to 20° C., 700 ml of water were added, and at a temperature of 35–40° C., 118 g of sodium hydroxide solution (32%) were added dropwise to adjust the pH to 8.0. The product which had precipitated out was filtered off with suction at 20° C. and dried overnight at 60° C. in a vacuum drying cabinet. This gave 200.3 g (89%) of n-nonanoylamidocaproyloxybenzenesulfonic acid, sodium salt as a white solid. The following analytical data for the product were determined by means of HPLC:

93.9% of n-nonanoylamidocaproyloxybenzenesulfonic acid, sodium salt 0.7% of n-nonanoylamidohexanoic acid 0.5% of p-phenolsulfonic acid, sodium salt 0.4% of nonanoyloxybenzenesulfonic acid, sodium salt Examples 8 to 10 describe the synthesis of n-decanoylamidocaproyloxybenzenesulfonic acid, sodium salt using various solvents and various conditions during work-up.

8. Synthesis of n-decanoylamidocaproyloxybenzenesulfonic acid, sodium salt in toluene 142.7 g (0.5 mol) of n-decanoylamidohexanoic acid and 98.1 g (0.5 mol) of p-phenolsulfonic acid, sodium salt (100%) were suspended in 400 ml of toluene and heated to 80° C. Over the course of 4 hours, 62.5 g (0.525 mol) of thionyl chloride were added dropwise to this mixture, which was then stirred for a further 2 hours at 80° C. Then, 15.0 g of sodium hydroxide microprills were added, and the mixture was diluted by subsequently stirring with toluene. The reaction product which had been filtered off with suction was stirred into 500 ml of water, and the pH was adjusted to 7.5. After the mixture had again been filtered with suction, the product was washed with 2×150 ml of water and dried overnight at 50° C. in a vacuum drying cabinet. This gave 220.3 g (95%) of n-decanoylamidocaproyloxybenzenesulfonic acid, sodium salt as a white solid. The following analytical data for the product were determined by HPLC:

93.6% of n-decanoylamidocaproyloxybenzenesulfonic acid, sodium salt 0.1% of p-phenolsulfonic acid, sodium salt 1.3% of decanoyloxybenzenesulfonic acid, sodium salt 9. Synthesis of n-decanoylamidocaproyloxybenzenesulfonic acid, sodium salt in diethylene glycol dimethyl ether 74.1 g (0.25 mol) of n-decanoylamidohexanoic acid and 49.1 g (0.25 mol) of p-phenolsulfonic acid, sodium salt (100%) were introduced into 375 ml of diethylene glycol dimethyl ether. Over the course of 3 hours, 32.7 g (0.275 mol) of thionyl chloride were added dropwise thereto, and the mixture was then stirred for 3 hours at the same temperature. The reaction product was filtered off with suction at room temperature, washed with 100 ml of diethylene glycol dimethyl ether and dried at 30° C. under reduced pressure. The crude product was neutralized in 250 ml of water with 20 g of sodium hydroxide solution (33%), again filtered with suction, washed with 3×50 ml of water and dried at 30° C. under reduced pressure. This gave 84.4 g (73%) of n-decanoylamidocaproyloxybenzenesulfonic acid, sodium salt as a beige-white solid. The following analytical data for the product were determined by means of HPLC:

94.7% of n-decanoylamidocaproyloxybenzenesulfonic acid, sodium salt 0.2% of p-phenolsulfonic acid, sodium salt 0.3% of decanoyloxybenzenesulfonic acid, sodium salt 10. Synthesis of n-decanoylamidocaproyloxybenzenesulfonic acid, sodium salt in toluene using sodium carbonate for neutralization 142.7 g (0.5 mol) of n-decanoylamidohexanoic acid and 98.1 g (0.5 mol) of p-phenolsulfonic acid, sodium salt (100%) were introduced into 400 ml of toluene and heated to 80° C. over the course of 4 hours, 60.7 g (0.51 mol) of thionyl chloride were added dropwise to this mixture, which was then stirred for a further 2 hours at 80° C. 10.6 g of sodium carbonate were then added and the mixture was stirred for 30 minutes. The reaction mixture was filtered off with suction and stirred into 500 ml of water. Sodium hydroxide solution (33%) was used to adjust the pH to 7.5, and the mixture was again filtered with suction. The residue was washed with 2×150 ml of water and dried in a vacuum drying cabinet to give 221.4 g (96%) of n-decanoylamidocaproyloxybenzenesulfonic acid, sodium salt as a beige-white solid. The following analytical data for the product were determined by means of HPLC:

92.8% of n-decanoylamidocaproyloxybenzenesulfonic acid, sodium salt 0.3% of p-phenolsulfonic acid, sodium salt 1.5% of decanoyloxybenzenesulfonic acid, sodium salt

What is claimed is:

1. A process for the preparation of amido acid phenyl esters of the formula I

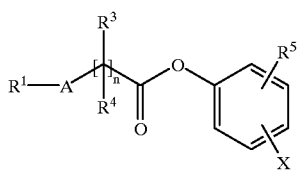

(I)

where

A is a group of the formula —CONR$^2$— or —NR$^2$CO—,

R$^1$ is an alkyl, alkenyl, alkynyl or cycloalkyl group having in each case from 1 to 26 carbon atoms, or an aryl or alkylaryl group having in each case from 6 to 14 carbon atoms, R$^2$ is hydrogen or an alkyl, alkenyl, alkynyl or a cycloalkyl group having in each case from 1 to 26 carbon atoms, or an aryl or alkylaryl group having in each case from 6 to 14 carbon atoms, R$^3$ and R$^4$ may be identical or different and can each be hydrogen or an alkyl, alkenyl, alkynyl or a cycloalkyl group having in each case from 1 to 10 carbon atoms, R$^5$ is hydrogen, halogen or an alkyl, alkenyl, alkynyl, cycloalkyl or an alkoxy group having in each case from 1 to 6 carbon atoms, n is a number from 1 to 10, X is a group of the formulae SO$_3$M, OSO$_3$M, (CH$_2$)$_m$SO$_3$M, (CH$_2$)$_m$O-SO$_3$M, CO$_2$M and N(R$^6$)$_3$Y, where M is hydrogen or an alkali metal ion, R$^6$ is an alkyl group having from 1 to 6 carbon atoms or a cycloalkyl group having from 4 to 6 carbon atoms, Y is a halogen atom and m is 1 or 2, which comprises adding an inorganic acid halide to a mixture of the compounds of the formulae II and III

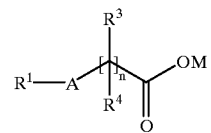

(II)

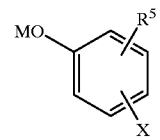

(III)

where A, R$^1$, R$^2$, R$^3$, R$^4$, R$^5$, X and M are as defined above.

2. The process as claimed in claim 1, which is carried out using a molar ratio of the compounds II and III of 1:0.7 to 1.5.

3. The process as claimed in claim 1, which is carried out using a molar ratio of the compounds II and III of 1:0.8 to 1.3.

4. The process as claimed in claim 1, which is carried out in the presence of an organic solvent.

5. The process as claimed in claim 1, which is carried out in the presence of toluene, xylene, benzene, monoglyme, diglyme, diisopropyl ether, tetrahydrofuran, dioxane, isobutyl methyl ketone, acetone, diethyl ketone, acetonitrile, carboxylic alkyl esters or mixtures thereof.

6. The process as claimed in claim 1, which is carried out in carboxylic alkyl esters or toluene as solvent.

7. The process as claimed in claim 1, wherein the amount of acid halide is from 0.5 to 2 molar equivalents, based on amidocarboxylic acid II.

8. The process as claimed in claim 1, wherein the amount of acid halide is from 0.7 to 1.5 molar equivalents, based on amidocarboxylic acid II.

9. The process as claimed in claim 1, wherein the amount of acid halide is from 0.9 to 1.4 molar equivalents, based on amidocarboxylic acid II.

10. The process as claimed in claim 1, which is carried out at from 25 to 120° C.

* * * * *